(12) United States Patent
Foote

(10) Patent No.: US 9,752,965 B2
(45) Date of Patent: Sep. 5, 2017

(54) APPARATUS AND METHOD FOR FAST SAMPLING AND MEASUREMENT

(71) Applicant: Sensigent LLC, Baldwin Park, CA (US)

(72) Inventor: Steven R Foote, Temecula, CA (US)

(73) Assignee: SENSIGENT LLC, Baldwin Park, CA (US)

( * ) Notice: Subject to any disclaimer, the term of this patent is extended or adjusted under 35 U.S.C. 154(b) by 250 days.

(21) Appl. No.: 14/513,514

(22) Filed: Oct. 14, 2014

(65) Prior Publication Data

US 2015/0101392 A1    Apr. 16, 2015

Related U.S. Application Data

(60) Provisional application No. 61/891,889, filed on Oct. 16, 2013.

(51) Int. Cl.
*G01N 1/14* (2006.01)
*G01N 1/24* (2006.01)

(52) U.S. Cl.
CPC .............. *G01N 1/14* (2013.01); *G01N 1/24* (2013.01)

(58) Field of Classification Search
CPC .......... G01N 1/14; G01N 1/2226; G01N 1/24; G01N 2033/0081; B07C 5/34; B07C 5/3408
See application file for complete search history.

(56) References Cited

U.S. PATENT DOCUMENTS

| | | | |
|---|---|---|---|
| 3,321,954 A * | 5/1967 | Bailey | G01N 1/2226 73/1.03 |
| 4,909,090 A | 3/1990 | Mcgown et al. | |
| 5,305,887 A | 4/1994 | Krieg | |
| 5,325,705 A | 7/1994 | Tom | |
| 5,361,912 A | 11/1994 | Krieg | |
| 5,376,550 A * | 12/1994 | Fine | B07C 5/34 209/3.1 |
| 5,405,014 A | 4/1995 | Krieg | |
| 5,520,060 A | 5/1996 | Gysi et al. | |
| 5,558,836 A * | 9/1996 | Rounbehler | G01N 21/9018 356/218 |
| 5,571,978 A | 11/1996 | Gysi et al. | |
| 6,099,659 A | 8/2000 | Tacito et al. | |
| 6,533,124 B1 | 3/2003 | Tacito et al. | |
| 7,208,123 B2 | 4/2007 | Knollenberg | |
| 7,971,470 B2 | 7/2011 | Broz | |

* cited by examiner

*Primary Examiner* — Blake A Tankersley
(74) *Attorney, Agent, or Firm* — Carrie Marlene Stroup

(57) ABSTRACT

Sampling systems for use on production lines with the capability to measure chemical components of a gas, vapor, or liquid sample taken from a product on the line and at a faster rate than the individual sensors alone are capable of. In one embodiment, the system detects the presence of insoluble hydrocarbons in the gas vapor present inside refillable water bottles that have been returned by the consumer. Each sampling system—apparatus—comprises two or more sub-systems each comprising: one or more sensors for performing a measurement of interest on a gas, vapor, or liquid sample, valves and a pump for directing the flow of samples, optionally an enclosed volume to hold the sample, and all under the direction of a control system. The sampling system also automatically acts on the measurement to detect when defective goods have reached a point where they can be ejected from the production line.

14 Claims, 16 Drawing Sheets

APPARATUS AND METHOD FOR FAST SAMPLING AND MEASUREMENT

PRIORITY CLAIM

This application claims priority to Provisional U.S. Ser. No. 61/891,889 filed Oct. 16, 2013. The entire contents of the aforementioned application are hereby directly incorporated in by reference.

BACKGROUND OF THE INVENTION

Field of the Invention

The present invention relates generally to an apparatus that is able to provide measurements at the rate required for a production line using sensors that are individually slower than the rate required to match the rate of the production line.

Description of the Related Art

Measurements of parameters of interest in gasses or liquids are commonly desired on goods being produced for sale on a production line running at a high rate of speed. One problem often faced is that the sensors capable of performing the desired measurement accurately, reliably and economically may require a time to perform the measurement that is longer than the time available at a point on the production line. When this situation occurs the measurement cannot be taken without reducing the speed of the production line which increases the costs of production. Alternatively a more expensive sensor may be employed for the measurement which also increases the costs of production. Therefore it would be desirable to have a way to utilize the preferred sensor in a manner that enables the production line to produce goods at the maximum possible rate.

There is more than one method to address this problem currently in use but all have deficiencies. One method currently used to utilize the preferred sensor in a manner that enables the production line to produce goods at the maximum possible rate is to divide the production line and utilize multiple sensors. Briefly, this method splits the production line into parallel segments, each operating at a correspondingly slower rate of production, and each utilizing the one of the preferred sensors to perform a measurement. This has the disadvantage of requiring multiple segments of the production line, each typically requiring costly production equipment to be dedicated to it.

Another method currently used to utilize the preferred sensor in a manner that enables the production line to produce goods at the maximum possible rate is to create a circular path for the goods being produced that causes the goods to stay in the same general location for a longer period of time. During this longer period of time a plurality of sensors to perform the desired measurement can be employed. This method also has the disadvantage of requiring costly production equipment to be dedicated to it to create the circular path and move the goods along the circular path.

There is currently no apparatus to utilize a preferred sensor requiring a measurement time longer than the time available at a measurement point on the production line in a manner that enables the production line to produce goods at the maximum possible rate without additional production equipment cost. Referenced U.S. Pat. No. 5,305,887 issued to Krieg, et al. describes an apparatus that utilizes two or more sensors to perform a measurement simultaneously; however the apparatus disclosed requires a circular path with an inner and outer track for the separate measurement sensors thus adding costly production equipment to perform the measurement.

Existing methods of utilizing a preferred sensor requiring a measurement time longer than the time available at a measurement point on the production line in a manner that enables the production line to produce goods at the maximum possible rate all require costly additional production equipment or require the speed of the production line to be reduced. Thus there is a need for an apparatus that would provide a capability to measure a characteristic of a gas or liquid sample at a faster rate than the sensors alone are capable of.

SUMMARY OF THE INVENTION

The present disclosure comprises various embodiments of a sampling system for use on production lines, with the capability to measure a characteristic of a gas or liquid sample taken from a product on the line and at a faster rate than the individual sensors alone are capable of. In one embodiment, the system detects the presence of insoluble hydrocarbons in the gas vapor present inside refillable water bottles that have been returned by the consumer. Each sampling system, or apparatus, comprises two or more sub-systems with each sub-system comprising: one or more sensors for performing a measurement of a parameter or chemical component a gas or liquid sample, valves and a pump for directing the flow of samples, optionally an enclosed volume to hold the sample, and all under the direction of a control system. The sampling system also automatically acts on the measurement to detect when defective goods have reached a point where they can be ejected from the production line.

In the production of goods for commerce, there are many occasions when it is advantageous to make a measurement of the composition of a gas or liquid that is part of, or associated with, the goods being produced. For example, in the bottled water industry there is a need to measure the composition of the gas vapor present inside refillable water bottles that have been returned by the consumer for re-filling. In this case the goal is to measure any vapor present that is not a component of clean air so that bottles that are contaminated (e.g. with insoluble hydrocarbons) can be removed from the production line before contaminating the bottling equipment. Another example is the vapor measurement of odorant added to a product such as detergent to insure the correct type and amount are present. In general the purpose of making the measurement is to either verify the correct quantity of a desired component is present, or to verify the absence of an undesired component.

Due to the above mentioned problems, a need exists for an apparatus to measure a characteristic of a gas or liquid sample at a faster rate than the sensors within the apparatus alone are capable of. Thus, an object of the present invention is to provide an apparatus that will overcome the problems and disadvantages of the prior art approaches described above.

A further object of the various embodiments presented herein is to provide an apparatus to measure a characteristic of a gas or liquid sample at a faster rate than the sensors alone are capable of without requiring costly additional production equipment such as conveyers or rotary tables.

It is a further object of the various embodiments to provide an apparatus to measure a characteristic of a gas or liquid sample at a faster rate than the sensors alone are capable of and to provide an automatic capability to accept or reject from the production line particular goods being produced based on the measurement taken.

It is also an object of the present invention to provide an apparatus and method that can be readily extended to a greater numbers of sensors to accommodate higher production line rates. Each apparatus may comprise one or more sensors; and, a sampling system would consist of one or more, or two or more of such apparatuses under the operational control of a single control system or multiple control systems that cooperate with each other.

To accomplish these and other objects, a sampling system (i.e. an apparatus) is provided that can be positioned at one point on the production line, and possesses two or more sub-systems as exemplified by FIG. 1 and FIG. 11. Each sub-system of the apparatus comprises one or more sensors for performing a measurement of interest on a gas, vapor or liquid sample, and optionally an enclosed volume capable of capturing a sample of gas or liquid within a short time period, for example less than one second. Each sub-system also comprises other associated components, such as valves and a pump to direct the flow of the sample. The sampling system then provides the sample to a sensor and associated components selected from a plurality of sensors and associated components in order to perform the desired measurement of one or more components in the sample. The sampling system may additionally and automatically act on the measurement by means of a detector that detects when defective goods corresponding to a particular measurement have reached a point where they can be ejected from the production line, if desired.

In one embodiment (e.g. FIGS. 1-5), the sampling system, or apparatus, comprises at least two subsystems, wherein each subsystem comprises: a control system directing the operation of: one sensor to detect a chemical component of a gas or liquid sample; an enclosed volume acting as a reservoir to hold the sample before it is tested (optional); a pump to circulate the sample over the sensor; and a plurality of valves to direct the flow of the product sample, or a reference (control) sample, into, through and out of the subsystem. The subsystem control system may also electronically communicate with the production line control system, such as to indicate the identity of a "tagged" product that has been identified by the subsystem sensor(s) as possessing the chemical component in question. The production line control system may then act to eject the tagged product downstream from the sampling system. A specific exemplification of this embodiment is disclosed herein for testing recycled drinking bottles for contamination (e.g. FIGS. 10-16).

This embodiment comprises a three phase method, and an optional fourth phase depending on the type of sensor, and comprising: a "fast sampling interval" (e.g. FIG. 2); a "measurement interval" (e.g. FIG. 3); a "purge or reference sample interval" (e.g. FIG. 4); an optional "recovery or reference interval" (e.g. FIG. 5).

During the "fast sampling" interval, a gas, vapor, or liquid sample derived from a product enters the subsystem from the production line. The sample inlet valve directs a product sample taken from a good (e.g. drinking bottle on the production line) to the enclosed volume (i.e. reservoir) and any excess sample is released out of the subsystem through the exhaust valve. The sample is pushed or pulled through the subsystem via either positive pressure applied to the inlet valve, or suction applied to the exhaust valve. The present invention separates the acquisition of the product sample from the time required to measure the composition of the sample. Since the purpose of separating these intervals is to allow for fast sampling to maintain the speed of production, then this phase is referred to as the "fast sampling interval", which lasts about 1 second.

Measurement Interval:

The measurement interval occurs after the fast sampling interval, and it is the period required by the sensor to measure the chemical composition of the gas, vapor or liquid sample stored in the enclosed volume during the fast sampling interval. Because the product sample is already in the subsystem from the fast sampling interval, then the sample inlet valve, purge inlet valve and exhaust valve are closed throughout the duration of the measurement interval. The subsystem pump operates to circulate the product sample through a closed loop comprising the directional valves and the sensor for detecting the components of the sample. The time required for the measurement is largely a function of the type of sensor; therefore, the subsystem also comprises a means to eject a tagged product that is located a distance sufficiently downstream for the sensor to complete the analysis and convey the results to the subsystem control system, which subsequently conveys the information to the means to eject products from the line.

Purge or Reference Sample Interval (Optional):

This interval is for the introduction of the purge or reference sample; and, it is not used for sensors that do not require a recovery period or a reference sample between measurements. During the introduction of the purge or reference sample, some valves are open to allow the purge or reference sample to fill as much of the system volume as possible, while the sample inlet valve and the exhaust valve are closed.

Recovery or Reference Interval (Optional):

The recovery or reference interval is a period required by many sensors to either recover to a known state after making a measurement or to measure a known reference value (i.e. control sample) as a means of next measuring an unknown value—(i.e. re-calibrate the sensor before testing each product sample). In the present invention this interval includes the time required to purge the previous sample from the part of the apparatus being described and to re-circulate the purge or reference sample a sufficient time for the particular sensor being used.

In another embodiment (e.g. FIG. 6), three apparatuses of FIG. 1 architecture are combined to make a "three sensor system" in an example of increasing the measurement speed by a factor of three as compared to the embodiment of FIG. 1 operating alone.

In another "cost effective" embodiment (e.g. FIGS. 7-8), the apparatus comprises two or more sensors, and four or more valves under the direction of a control system. This configuration requires the measurement time to be equal to the sensor measurement time, so no increase in speed is gained in the measurement time. However, many sensors require a purge or recovery period and utilizing multiple sensors can still provide an increase in effective measurement rate by eliminating the purge or recovery period from the effective measurement cycle.

Another embodiment comprises an exemplification for testing of gas and vapor contaminates in bottles being filled with drinking water on a production line (e.g. FIGS. 10-16). The system can sample each bottle within one second, allowing the bottle to proceed down the production line, and produce an output classifying the bottle as clean or contaminated within 4 seconds of the bottle being sampled. The system may comprise, for example, 10 gas contamination sensors, such as an apparatus comprising 10 subsystems of the embodiment of (FIG. 11), and lying in parallel on the production line under the direction of one or more control systems.

The method of this bottling embodiment may comprise the following steps: a fast sample interval during which the sample is introduced into the enclosed volume while the gas sensor and pump re-circulate the purge air; a measurement interval during which the sample is re-circulated through the gas sensor and the enclosed volume by the pump; an initial purge interval during which clean dry compressed air is introduced into the enclosed volume while the sample continues to re-circulate; a second purge interval during which clean dry compressed air is introduced into the balance of the pneumatic system; and, a purge or reference sample interval during which clean dry purge air is re-circulated through the gas sensor and enclosed volume by the pump. This cycle then repeats as many times as desired.

Numerous other objects and advantages of the present invention will be apparent to those skilled in this art from the following description wherein there is shown and described a preferred embodiment of the present invention simply by way of illustration of one of the modes best suited to carry out the invention. As will be realized, the invention is capable of other different embodiments, and its several details are capable of modification in various obvious aspects without departing from the invention. Accordingly, the drawings and descriptions should be regarded as illustrative in nature and not restrictive.

BRIEF DESCRIPTION OF THE DRAWINGS

The present invention will become more clearly appreciated as the disclosure of this invention is made with reference to the accompanying drawings. In the drawings.

DETAILED DESCRIPTION OF THE PREFERRED EMBODIMENT

Disclosed herein are various embodiments of sampling apparatuses, systems, and their methods of use to measure a characteristic of a gas or liquid sample at a faster rate than individual sensors alone are capable of. Various embodiments of the sampling apparatuses and systems will now be described with reference to FIGS. 1 to 17 of the accompanying drawings.

System Architecture

Figure 1:
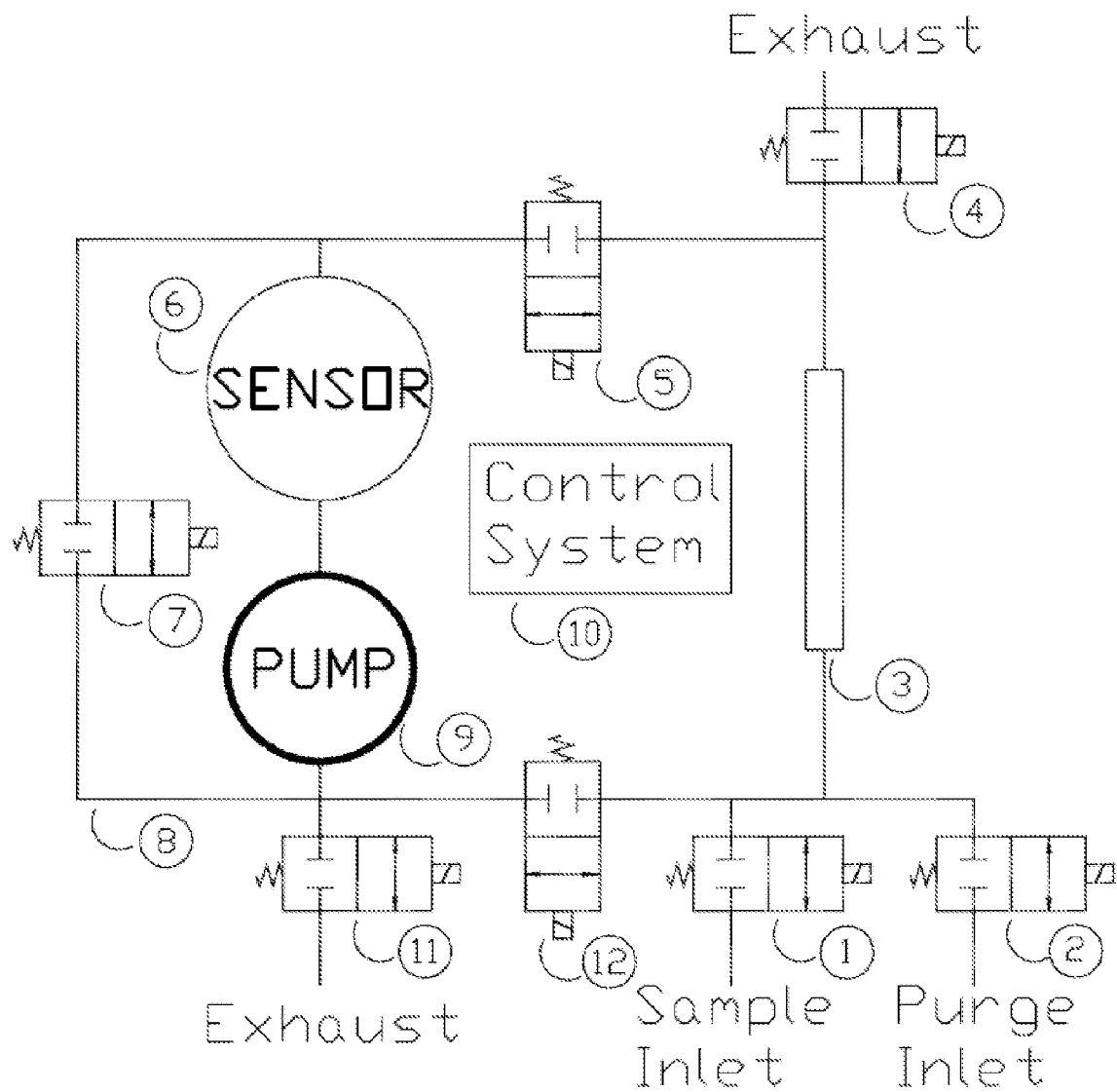
FIG. 1 is a block diagram of the sub-system of the apparatus for one embodiment used in the method of FIGS. 2-5 comprising one sensor, one pump, seven valves, a reservoir to hold a sample of gas, vapor or liquid extracted from a product on a production line, and all under the operational control of a control system.

FIG. 1 is a schematic of one embodiment of part of the apparatus (i.e. "a sub-system" of the apparatus), comprising: one sensor, one pump, seven valves, a reservoir to hold a sample of gas, vapor or liquid extracted from a product on a production line, and all under the operational control of a "control system" 10 Although the block diagram is of a single sensor and its associated components, a functioning apparatus (i.e. "system") would consist of two or more such parts of the apparatus under the operational control of a single control system (not shown) or multiple control systems, such as one control system 10 per apparatus.

Referring to FIG. 1, the valves 1 and 2 control the input of either a sample or a reference gas or liquid into the system from the production line. Valve 4 provides an exhaust during the fast sampling phase during which the enclosed volume 3 is filled with the gas or liquid to be sampled. Valves 5 and 12 control the input of a gas or liquid contained in the enclosed volume 3 to the sensor 6. During the measurement interval the gas or liquid is circulated over the sensor by pump 9. Valves 2, 5, 7 and 11 are opened to purge the system or as part of a recovery period during which the sensor is exposed to a reference sample. The control system 10 controls the opening and closing of the valves and also provides control signals to the sensor 6 and pump 9 as required for their operation. Pipe or tubing 8 connects the apparatus's components together so that the sample of fluid or gas can flow under the direction of the control system 10.

In one embodiment the control system 10 contains a computer central processing unit, program memory, variable memory and various input and output circuits for sensing, controlling, and communicating with elements of the apparatus as needed. Alternatively the control system 10 could be created from either discrete digital elements or from analog circuit elements by those skilled in the art. The control system 10 may be a complete control system for one sensor operating in coordination with the control system for other systems by passing messages over a communication port such as an RS-232 serial port, an Ethernet port, an RS-485 Modbus port or any of a number of other communication ports common to industry and familiar to those skilled in the art. Alternatively, the control system 10 could be a portion of a single larger control system that controls the operation of all sensors and associated components in the entire apparatus.

Apparatus Components

Figure 11:
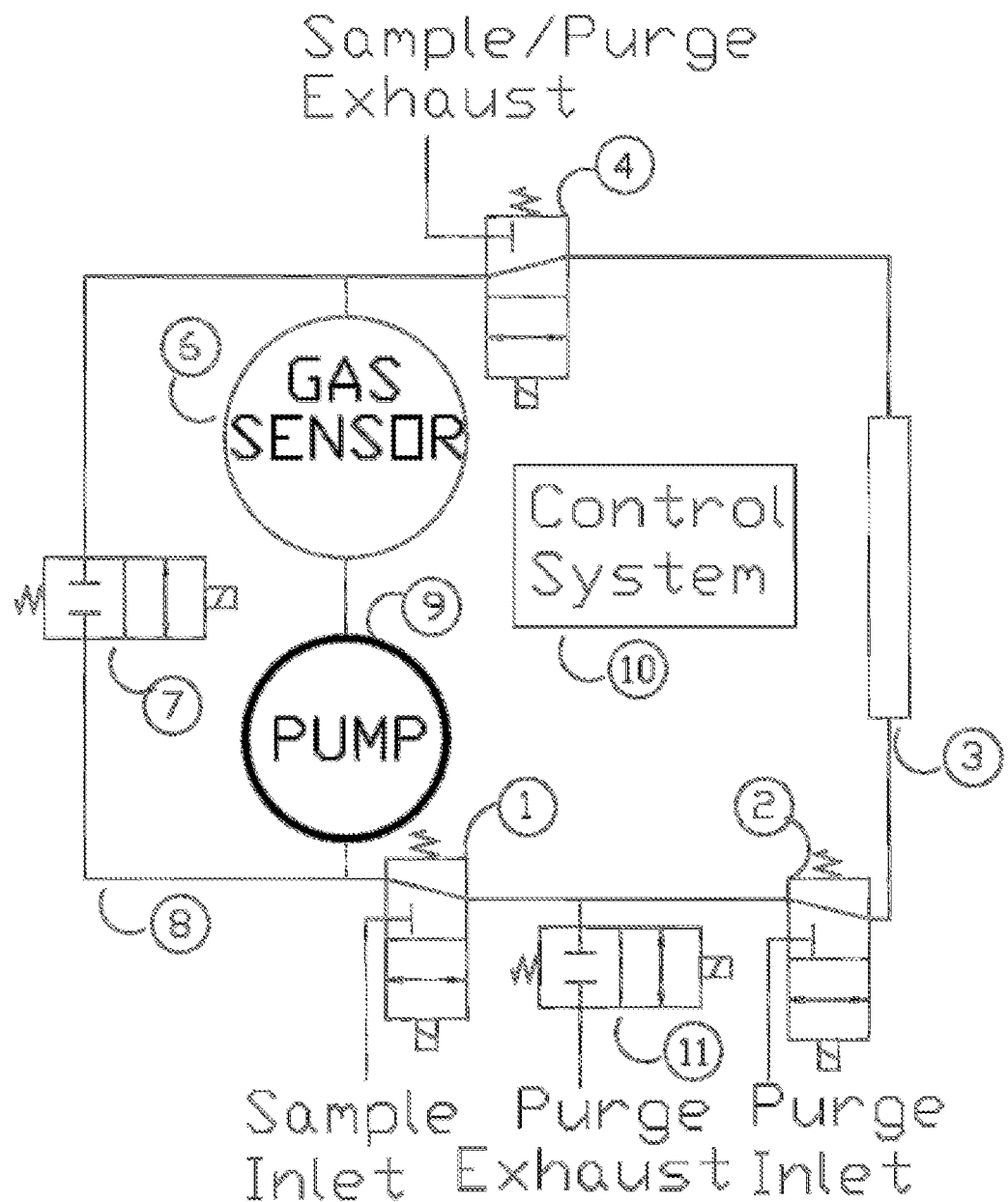
FIG. 11 is a block diagram of a subsystem of the apparatus used in the methods of FIGS. 12-15, in which each subsystem comprises one sensor, one pump, two one-way valves, four two-way valves, a reservoir to hold a sample of gas or liquid extracted from a product on a production line, and all under the operational control of a control system connected to the bottle of water in FIG. 10 for testing samples of gas in the bottle.

The types of sensors that could be utilized in the present invention include a large number of sensors for measuring chemical components of gases, vapors and liquids. It does not include sensors that measure parameters, such as temperature or flow rate. The purpose of measuring the chemical components of a sample is generally either to verify that the correct type and amount of a desired component is present or to verify the absence of an undesired component. A partial list of sensors that could be applied to the present invention include surface acoustic wave (SAW) sensors; quartz microbalance sensors; conductive composites; chemiresistors; metal oxide gas sensors such as tin-oxide gas sensors; organic gas sensors; field-effect transistors (MOSFET); piezoelectric devices; infrared sensors; humidity sensors; sintered metal-oxide sensors; Pd-gate MOSFET; metal FET structure; metal oxide sensors such as Taguchi gas sensors; phthalocyanine sensors; electrochemical cells; conducting polymer sensors; catalytic gas sensors; organic semi-conducting gas sensors; solid electrolyte gas sensors; piezoelectric quartz crystal sensors; dye-impregnated polymer films on fiber-optic sensors; polymer-coated micro-mirrors; electrochemical gas detectors; chemically sensitive field-effect transistors; carbon black-polymer composite chemiresistors; micro-electromechanical system devices; and micro-opto-electro-mechanical system devices and Langmuir-Blodgett film sensors. In particular the preferred embodiment of FIG. 11 is described in a configuration for use with a carbon black-polymer composite chemiresistor array comprising two or more sensors on a single miniature substrate an example of which is the CDM-516 contaminant detection system manufactured by Sensigent LLC.

The type of valves used in the present invention could be any type of gas, vapor or liquid valve able to be operated by an automatic control system, including valves operated by an electric solenoid, valves operated by pneumatic means and any other automatic valve. In one embodiment, the valves for use in the present invention comprise the electric solenoid operated valve model LHDA0531515H manufactured by the LEE company electro-fluidic systems group, or the electric solenoid operated valve model 648T011 NResearch Incorporated.

The types of pumps used in the present invention can be any type of pump capable of delivering the required volume of gas, vapor or liquid including rotary pumps and positive displacement piston or diaphragm type pumps an example of which is the model 2002 VD LC manufactured by Gardner-Denver Corporation.

The enclosed volume used in the present invention can be created in many different ways that are obvious to those skilled in the art. The primary requirement is that the volume be sufficient to supply an adequate sample of gas, vapor or liquid for a time period that is at least equal to the measurement interval. For example, if a particular sensor such as the CDM-516 manufactured by Sensigent LLC requires a sample gas flow volume of 1000 milliliters per minute and also requires a measurement interval of three seconds, then the enclosed volume for that sensor must be at least 1000*(3/60)=50 milliliters. One exemplary way to create the enclosed volume is to use a sufficient length of standard tubing which can be coiled up to reduce space. For example, 50 milliliters of stored volume can be enclosed in approximately 63 inches of tubing with 0.25 inch internal diameter. Other examples of enclosed volume would include any sort of gas, vapor or liquid tight tank or reservoir with an inlet and outlet port of whatever volume is required for a particular sensor.

The tubing required to connect the various components of the present invention can be of any type that is made of a material that is compatible with the gas, vapor or liquid sample, is mechanically strong enough to withstand the pressures and flows required for use with a particular sensor, and is able to be formed to make connections between the various other components within a reasonable space. An example of tubing that can be used with the CDM-516 sensor from Sensigent LLC and the other associated components is Tygon tubing with an internal diameter of 0.25 inch.

One advantage (of many) of the present invention is that suitable components for its various embodiment are sufficiently small to enable it to be realized in a space that enables it to be conveniently placed at a point on a production line. For example, the embodiment of FIG. 1 has been realized in a total volume of under 1000 cubic centimeters enabling ten such sub-systems to be combined into an apparatus in a space of approximately 10 liters, which is very small in relation to typical production line equipment.

Fast Sampling Interval

Figure 2:
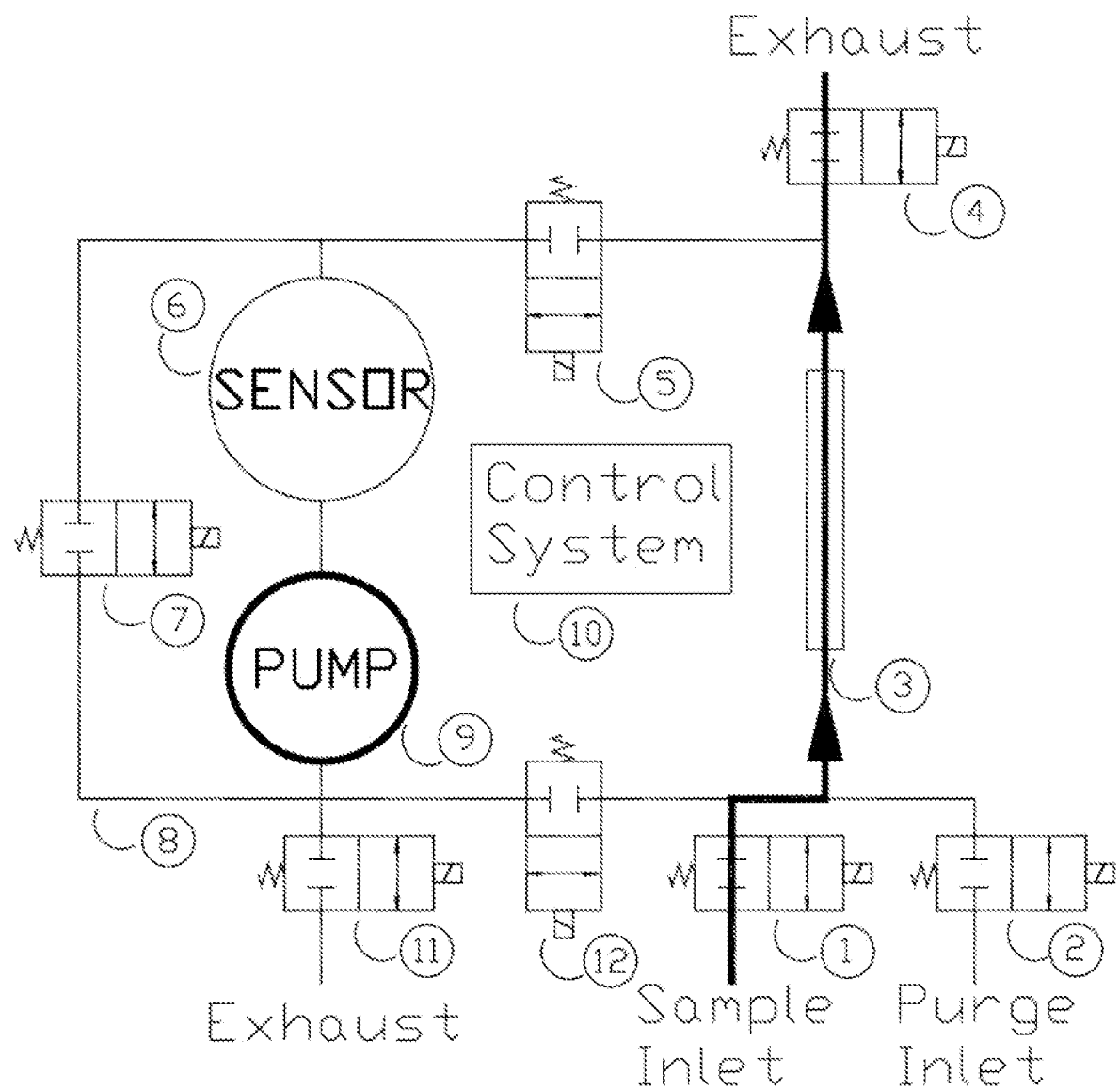
FIG. 2 is a block diagram of the subsystem of FIG. 1 with the gas, vapor or liquid sample flow illustrated during the "fast sampling interval" for the illustrated part of the apparatus during which the sample is being transferred to the selected enclosed volume.

The operation of the apparatus of FIG. 1 during the fast sampling interval is illustrated generally in FIG. 2. In this figure and all other figures depicting gas, vapor or liquid flow the thickened portion of the line indicates the portion with gas, vapor or liquid flow and the arrows indicate the direction of flow. During the fast sampling phase, valve 1 and valve 4 are opened to permit a sample to be quickly introduced into the enclosed volume 3 (e.g. the reservoir). The sample will be driven into the enclosed volume either by positive pressure from a compressed air system applied to the sample inlet port 1 or by a suction or vacuum from a vacuum pump applied to exhaust port 4 or some combination of these. Excess sample gas or liquid is allowed to escape to the exhaust by valve 4. The valves 5 and 12 are closed during the fast sampling interval to prevent disrupting the sensor 6 recovery period. Valve 11 is closed to prevent the escape of the purge or reference gas or liquid sample. Valve 7 is open to enable pump 9 to continue to circulate the purge or reference sample to the sensor 6.

The fast sampling interval as shown in FIG. 2 has the sample gas, vapor or liquid being driven through the system under external pressure; however, if needed a positive pressure pump could be added to the sample inlet 1, or a vacuum pump could be added to the exhaust port at valve 4 to accomplish the fast sampling process. The relative volume of the enclosed volume 3 compared to the volume of the pipe or tubing 8 connecting the other components is set to achieve a dilution that will allow the sensor 6 to detect the required level of gas, vapor or liquid in the sample. In general the relative volume of the pipe or tubing 8 will be small relative to the enclosed volume 3 so as to limit the dilution of the sample to less than 50%.

Measurement Interval

Figure 3:
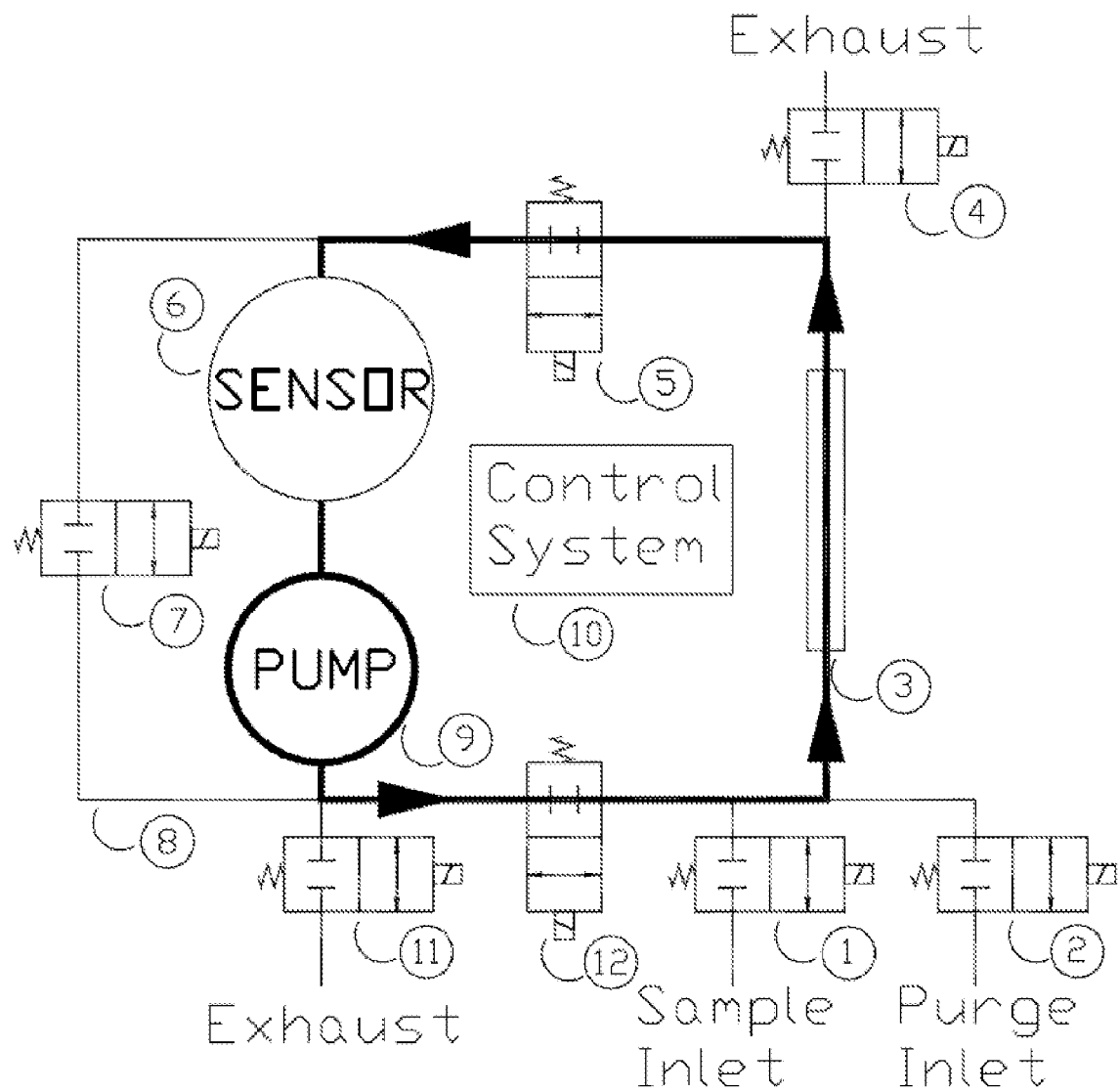
FIG. 3 is a block diagram of the subsystem of FIG. 1 with the gas, vapor or liquid sample flow illustrated during the measurement time interval for the illustrated part of the apparatus during which the sample is being transferred to the selected sensor for measurement.

The operation of the apparatus during the measurement interval is illustrated generally in FIG. 3. The valves 1 and 2 are closed since the sample of gas or liquid has already been acquired and the production line process can continue without waiting for the measurement to be completed. The valves 4, 7 and 11 are closed since there is no requirement to acquire a sample or purge air or a reference gas or liquid during the measurement interval. The valves 5 and 12 are open and the pump 9 is active so that the sample of gas or liquid acquired during the fast sampling phase is circulated over the sensor 6. Since the sample has already been acquired, then the actual measurement time of the sensor does not reduce the rate of the production line. The only requirement is that the mechanism for rejecting or selecting a product based on its measurement results is located at a point on the production line that allows sufficient time for the measurement to take place. For example if the measurement interval is three seconds and the production line is filling water bottles at a rate of one per second than the mechanism for rejecting contaminated bottles must be at least three bottles downstream of the measurement equipment.

Purge or Reference Sample Interval

Figure 4:
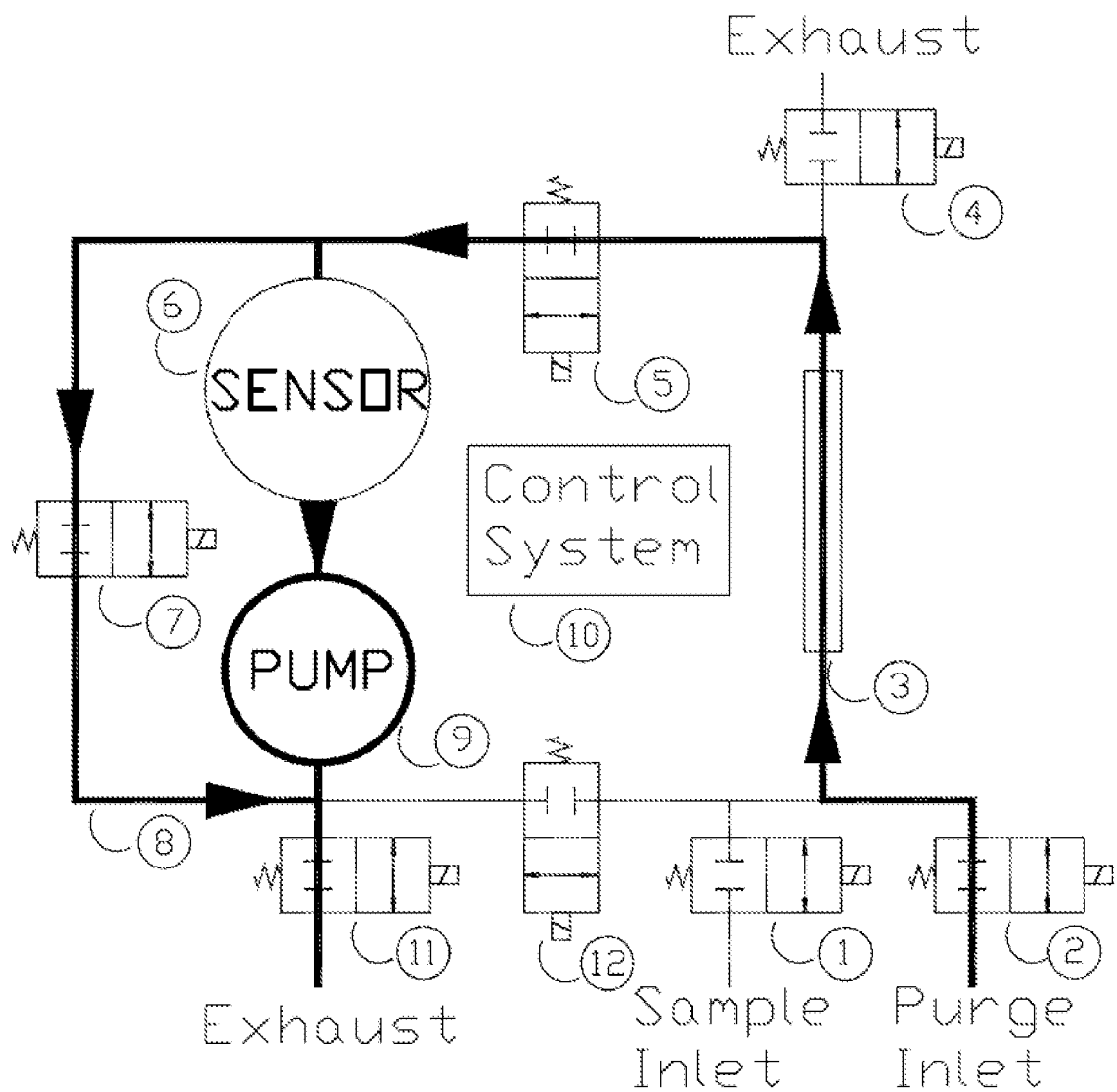
FIG. 4 is a block diagram of the subsystem of FIG. 1 during the purge or reference sample interval for the illustrated part of the apparatus during which a reference sample of a gas, vapor or liquid is being transferred to the selected enclosed volume.

The operation of the apparatus during the interval for the introduction of the purge or reference sample is illustrated generally in FIG. 4. It should be understood that this interval is optional and not required for sensors that do not require a recovery period or a reference sample between measurements. During the introduction of the purge or reference sample, valves 2, 5, 7 and 11 are open to allow the purge or reference sample to fill as much of the system volume as possible. Valve 4 is closed to force the purge or reference sample to flow through valve 5 rather than exhausting out of the system. Valve 12 is closed to prevent the possibility of an undesired reverse flow back through valve 7. Valve 1 is closed to prevent either the undesired introduction of a sample to the system or the undesired possibility of contaminating the sample being supplied to other sensors due to a reverse flow out through valve 1. During the interval for the introduction of the purge or reference sample, the enclosed volume 3 and the tubing or piping 8 is filled with the purge or reference sample to almost a maximum of its volume.

Recovery or Reference Interval

Figure 5:
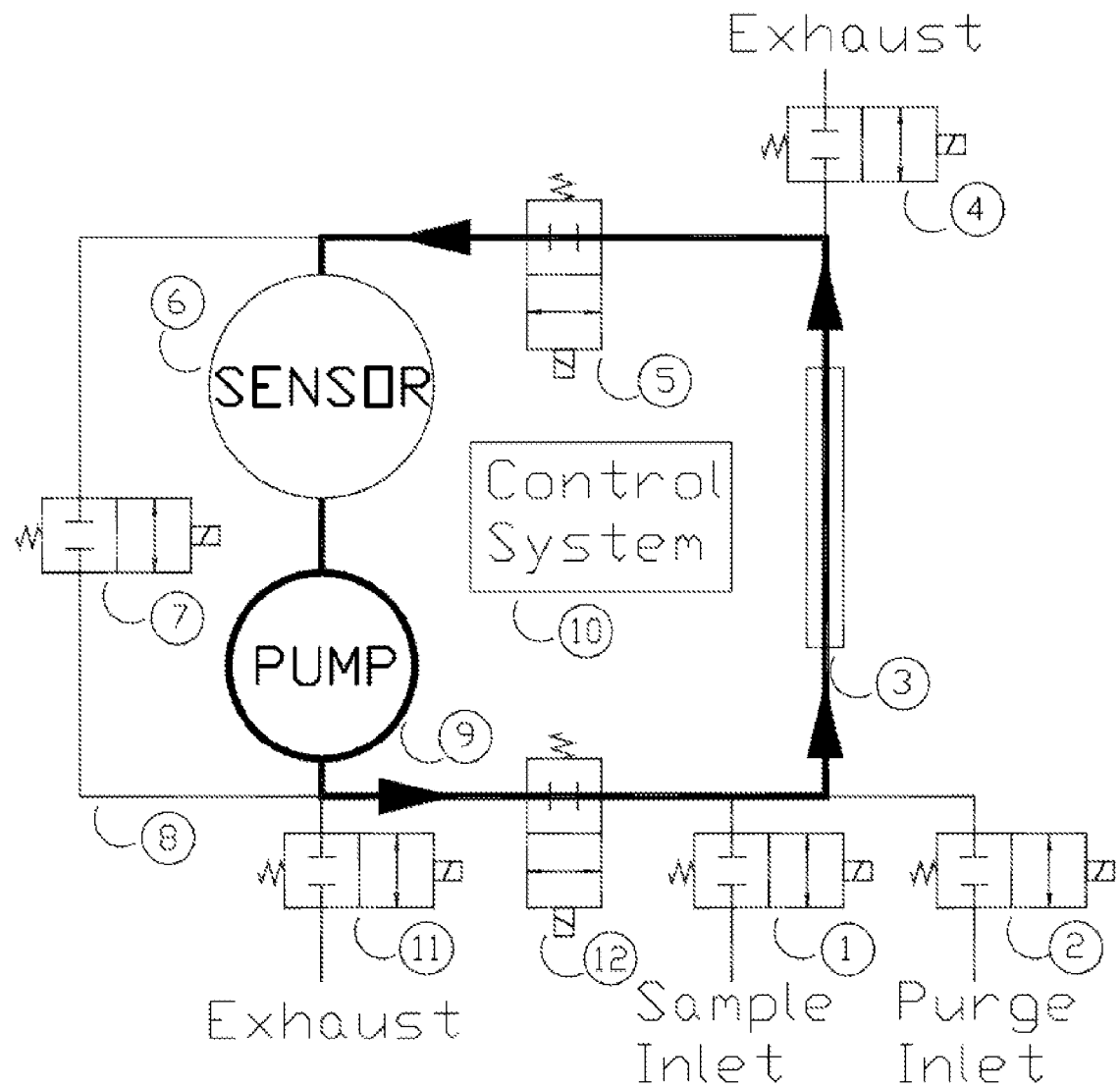
FIG. 5 is a block diagram of the subsystem of FIG. 1 during the recovery or reference interval for the illustrated part of the apparatus during which the gas, vapor or liquid reference sample is being transferred to the selected sensor for use as a baseline reference.

The operation of the apparatus during the recovery or reference interval is illustrated generally in FIG. 5. It should be understood that this interval is optional and it is not required for sensors that do not require a recovery period or reference sample between measurements. During this interval, the purge or reference sample is circulated over the sensor in generally the same way as a sample for measurement. The valves 1 and 2 are closed since the purge or reference sample of gas or liquid has already been acquired and the production line process can continue without waiting for the measurement to complete. The valves 4, 7 and 11 are closed since there is no requirement to acquire a purge air or a reference gas or liquid during the recovery or reference interval. The valves 5 and 12 are open and the pump 9 is active so that the purge or reference sample of gas, vapor or liquid acquired during the interval for the introduction of the purge or reference sample is circulated over the sensor 6. Since the measurement interval has already completed and the measurement result has been delivered to the production line equipment (e.g. computer control system), then the recovery or reference interval does not reduce the production rate. The only requirement is that there be a sufficient number of sensors incorporated into the system to insure that at least one sensor has completed the recovery or reference interval and is available for a fast sampling interval whenever the production line rate requires a new measurement. Therefore this invention allows the substitution of a larger number of slower sensors for a smaller number of faster sensors.

Three Sensor System

Figure 6:
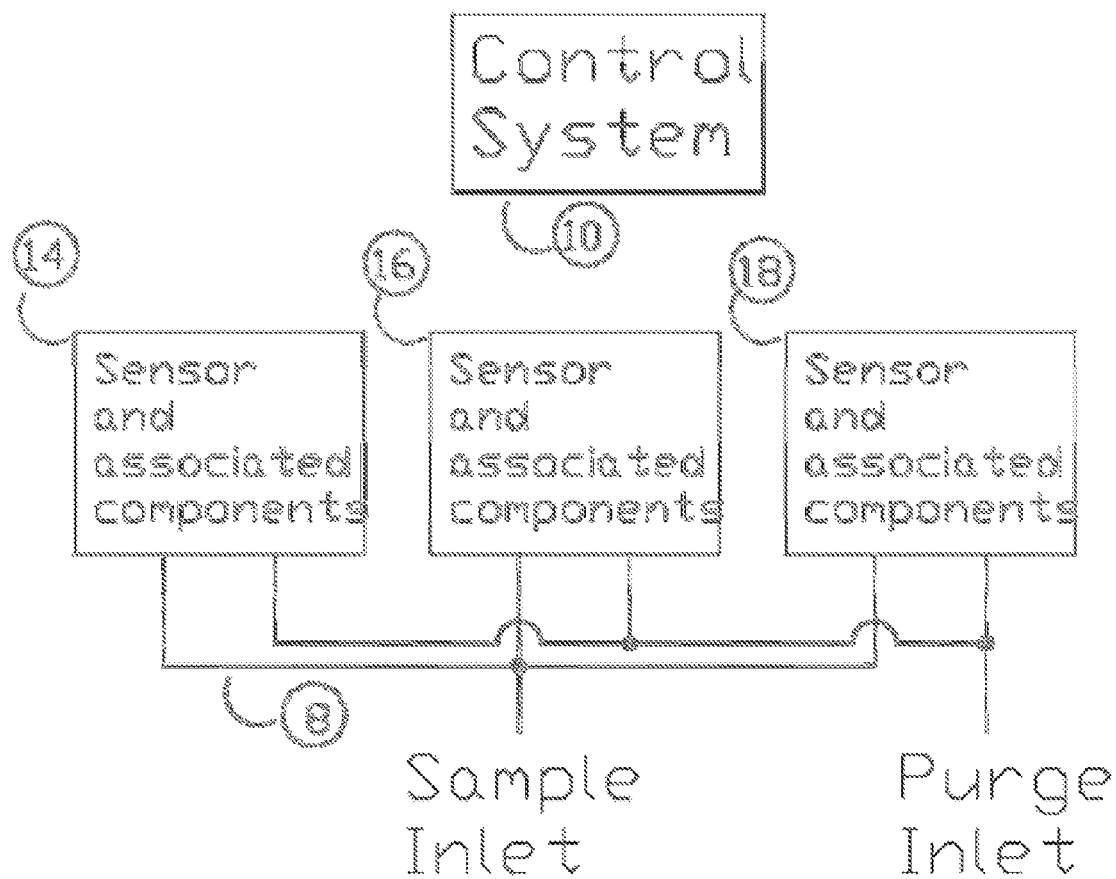
FIG. 6 is a block diagram of another embodiment of the apparatus showing three sub-systems per FIG. 1 comprising a total of three sensors and their associated components in an example of increasing the measurement speed by a factor of three as compared to one sub-system of FIG. 1 operating alone.

FIG. 6 illustrates a typical embodiment of the entire system incorporating three apparatuses of FIG. 1 operating with a control system 10. Within each apparatus (14, 16, and 18), each sensor 6 is connected to the single sample inlet by an associated valve 1 and connected to the purge inlet by an associated valve 2 through tubing 8 allowing each sensor and associated components to access either a sample or purge or reference gas or liquid sample under the control of the control system 10. By increasing the number of sensors and associated components, the effective measurement rate of the system or apparatus is only limited by the time required for the fast sampling interval, which is only limited by the flow rate of the sample though the tubing and into the enclosed volume.

Cost Effective Embodiment

Figure 7:
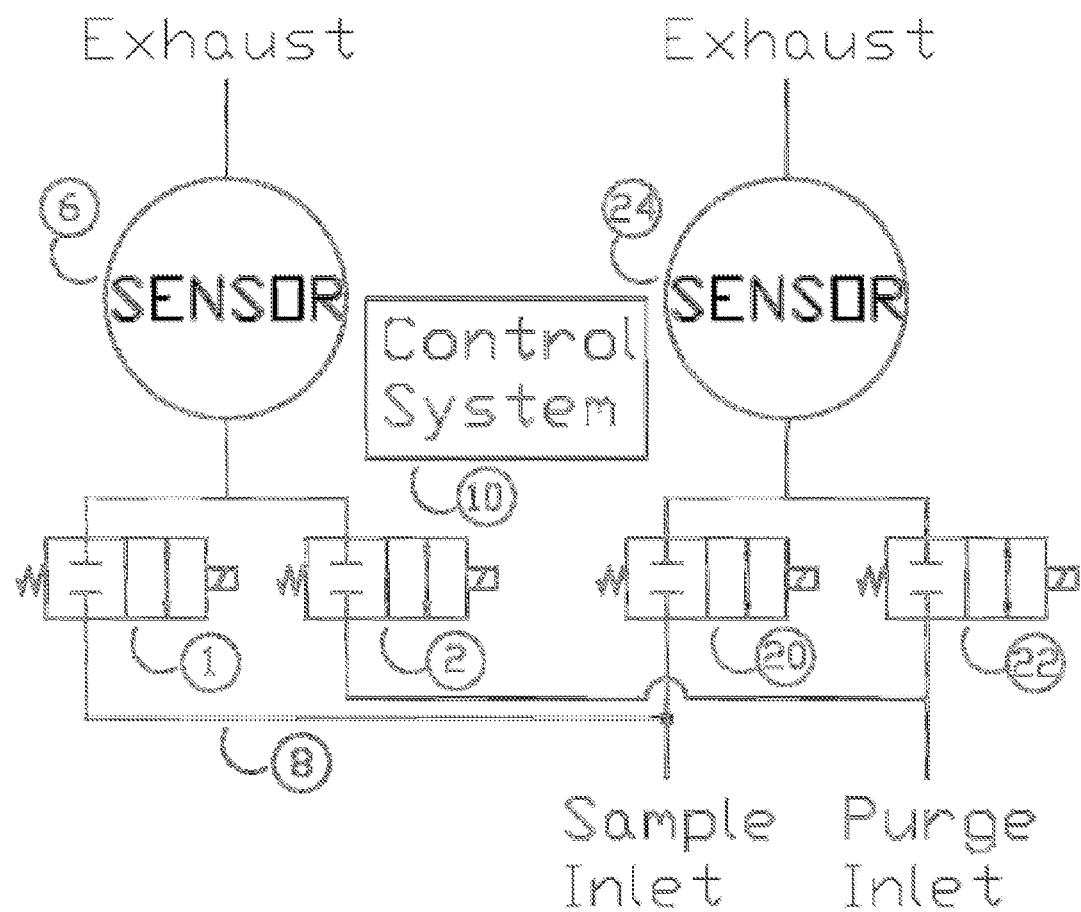
FIG. 7 is a block diagram of another "cost effective" embodiment of the apparatus comprising two sensors and its associated components in a lower cost configuration that omits the enclosed volume.

Another embodiment is illustrated in FIG. 7, and comprises a lower cost (as compared to FIG. 1 embodiment) configuration of a sampling apparatus and its method of its use for measuring samples of gas or liquid in products as they move along a production line, and at a faster rate than the sensors operating alone are capable of. In this embodiment the effective measurement interval is equal to the actual sensor measurement interval and is not reduced to only the time required for the fast sampling interval. However in this configuration the requirement for additional time for recovery or reference interval can still be eliminated.

As illustrated in FIG. 7, during a first measurement interval, valve 1 is open to allow a sample of gas or liquid to flow over sensor 6 and purge inlet valve 22 is open to allow a purge or reference sample to flow over sensor 6. On concluding the sample and measurement interval, i.e. the first measurement interval, the measurement result is delivered to the production equipment via control system 10 and valve 1 is closed. During the recovery and reference sample interval, i.e. the second measurement interval, valve 20 is open to allow a sample to flow over sensor 24 and valve 2 is open to allow a purge or reference sample to flow over sensor 6. On concluding the second measurement interval, the measurement result is delivered to the production equipment via control system 10 and valve 20 is closed.

If the recovery or reference interval is equal to or less than the sensor measurement interval, then two sensors are sufficient to reduce the effective measurement interval to the actual sensor measurement interval, rather than to the actual sensor measurement interval plus the recovery or reference sample interval.

If the recovery or reference sample interval is greater than the actual sensor measurement interval, then additional sensors can be added to this system to insure that there are a sufficient number of sensors incorporated into the system such that at least one sensor has completed the recovery or reference interval and is available for a measurement interval whenever the production line rate requires a new measurement. If the number of sensors used is equal to the recovery time divided by the measurement time rounded up to the next largest integer than the combination of all sensors and the control system function as a single sensor with no requirement for any purge or recovery time or reference sample time. Therefore this invention allows the substitution of a larger number of slower sensors for a smaller number of faster sensors.

Figure 8:
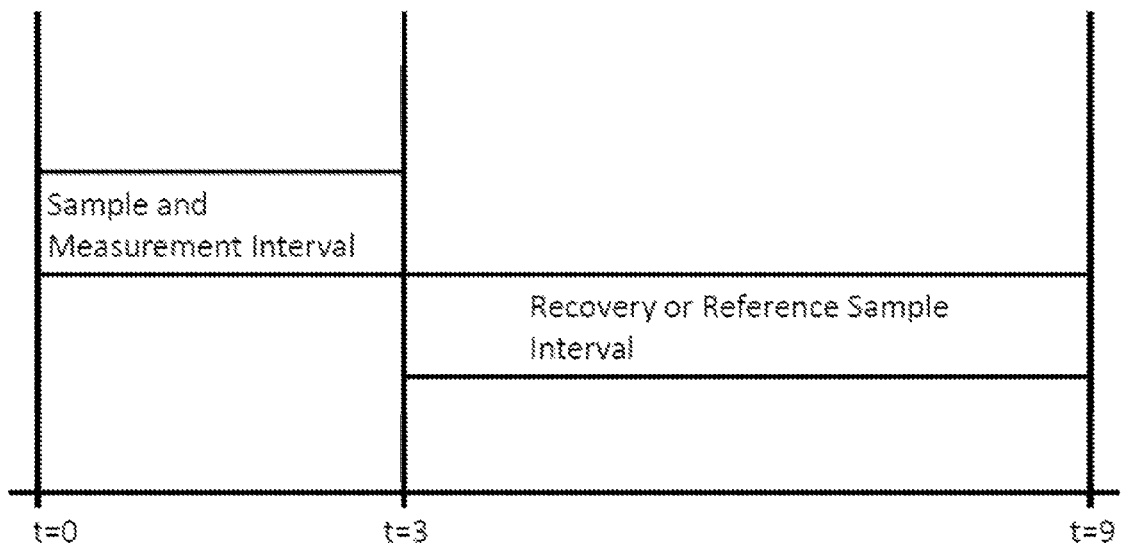
FIG. 8 is a time diagram showing the sequential operation of the lower cost configuration of the apparatus illustrated in FIG. 7.

FIG. 8 is a time diagram showing the sequential operation of the lower cost embodiment of the apparatus illustrated in FIG. 7. Because the lower cost configuration does not utilize an enclosed volume to store a measurement sample, then the sampling time and the measurement time are equal. In the case illustrated, the measurement time is 3 seconds. At 3 seconds the measurement is complete and results are available for the production equipment to take an action, such as rejecting a contaminated bottle. The sensor requires an additional 6 seconds of recovery or reference sample time, so at 9 seconds it is ready for use again under the direction of the control system 10. Therefore this configuration can achieve a maximum rate of one measurement every 3 seconds and will require 9 seconds for total cycle time. The total number of sensors needed is computed from the total cycle time in seconds (9) divided by the sample and measurement time (3 sec), which equals 3 sensors, and thus subsystems, to achieve this rate. The apparatus as shown if FIG. 7 can achieve a maximum rate of one measurement every 4.5 seconds since 9 seconds divided by 4.5 seconds equals a requirement for 2 sensors. Therefore, this particular cost effective apparatus with two subsystems that lack a reservoir for fast sampling can detect contaminants or verify product quality (e.g. detecting desired chemical component) at a rate of about one product per 5 seconds, which is slower than the apparatus of FIG. 1, as shown in FIG. 9.

Figure 9:
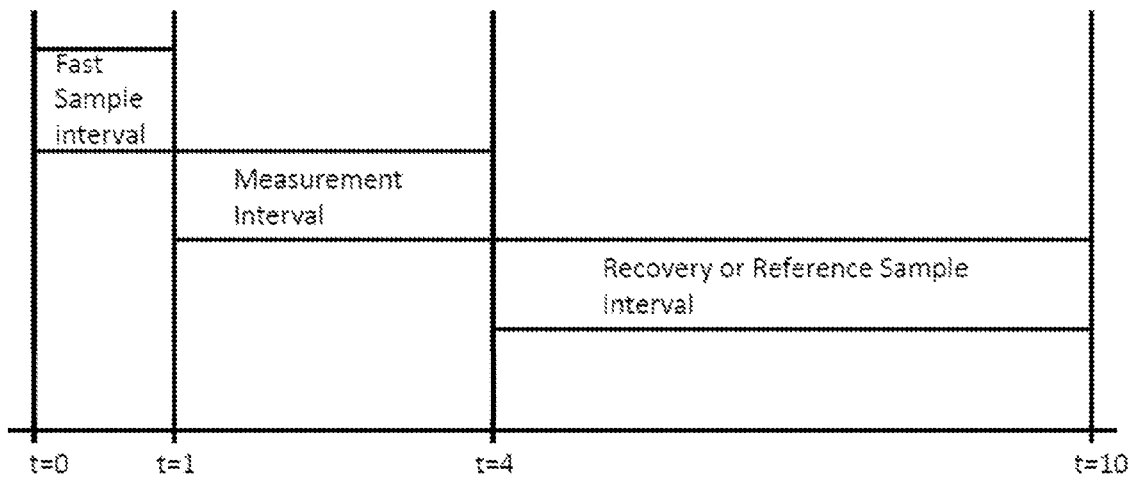
FIG. 9 is a time diagram showing the sequential operation of the configuration of the apparatus comprising two sub-systems of FIG. 1 operating in parallel.

By way of comparison, FIG. 9 is a time diagram showing the sequential operation of the embodiment of the apparatus illustrated in FIG. 1. Because this configuration utilizes an enclosed volume to store a measurement sample, then the sampling time and the measurement time are not necessarily equal. In the case illustrated the fast sampling time is one second and the measurement time is 3 seconds. At 4 seconds the measurement is complete and results are available for the production equipment to take an action, such as rejecting a contaminated bottle. The CDM-516 sensor requires an additional 6 seconds of recovery or reference sample time, so at 10 seconds it is ready for use again under direction of the control system shown 10. Therefore, this configuration can achieve a maximum rate of one measurement every 1 second and will require 10 seconds for the complete process—cycle time. The total number of sensors needed is computed from the total cycle time (i.e. fast sample time plus measurement time plus recovery or reference sample time) in seconds (10) divided by the fast sample time (1), which equals 10 sensors to achieve this rate. Since each subsystem as shown in FIG. 1 comprises one 1 sensor, then the apparatus would require 10 such subsystems operating under the direction of one control system 10, or multiple control systems 10 operating in coordination by exchanging signals or digital messages.

Exemplification

Testing Bottled Water for Gas Contaminates

Figure 10:
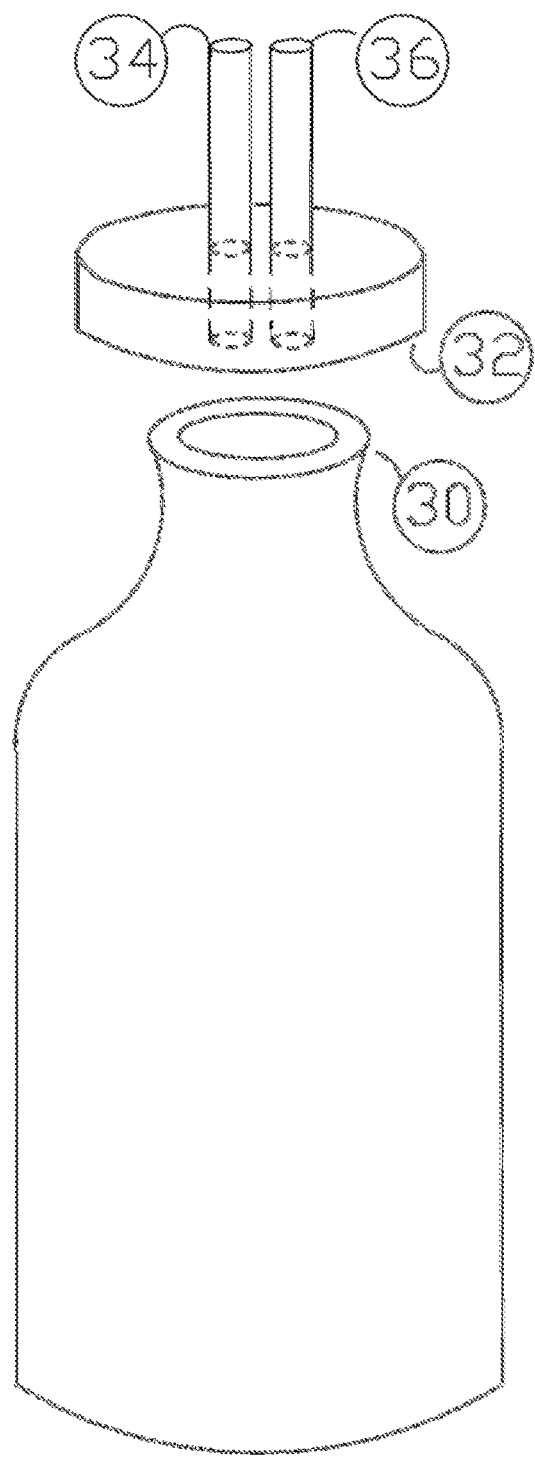
FIG. 10 is an illustration of a specific embodiment of a bottle of water on a production line being tested for contaminated gas.

FIG. 10 is an illustration of a specific embodiment of a bottle of water being tested for contaminated gas while on a production line for producing bottled water. The bottle is arranged so that resilient seal 32 is pressed against bottle 30 by either electrical or pneumatic means well known to those skilled in the art. The bottle may be either moving or stopped on the production line, and the seal will also be either moving or stopped. Once a seal has been achieved, then ports 34 and 36 are now in connection with the contents of the bottle and outside air is excluded. At this time a positive pressure can be introduced on either one of the ports, forcing a sample of the bottles contents from the other port which will be connected to the sample inlet 1. Alternatively, one port can be left open to the outside air and suction applied through the sampling path of the present embodiment as described supra to draw a sample from the bottle by suction. Typical contaminants that are of interest are hydrocarbons or urine residue that results from misuse of the refillable bottles by consumers.

FIG. 11 is an exemplification of one sampling apparatus connected to the bottle 30 of FIG. 10. and comprising a specific gas sensor, CDM-516, for detecting contamination in refillable water bottles. In this embodiment the sample inlet 1 is connected to one of the ports 34 or 36 on the sampling head shown in FIG. 10. This allows the gas contained within the bottle to be drawn by suction or pushed by pressure into the sample inlet 1, and the purge inlet 2 is attached to a source of clean dry compressed air for example a typical bottling plant compressed air system.

Figure 16:
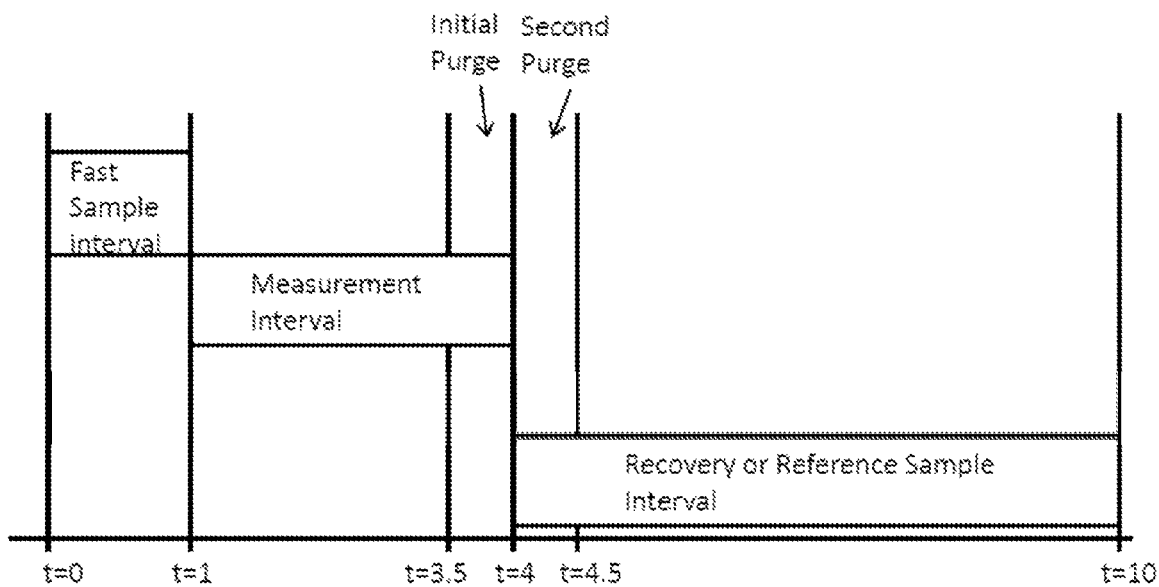
FIG. 16 is a time diagram showing the sequential operation of the configuration of the apparatus illustrated in FIG. 11.

This embodiment has the sequential operation shown in FIG. 16 consisting of a fast sample interval during which the sample is introduced into the enclosed volume while the gas sensor and pump re-circulate the purge air, a measurement interval during which the sample is re-circulated through the gas sensor and the enclosed volume by the pump, an initial purge interval during which the clean dry compressed air is introduced into the enclosed volume while the sample continues to re-circulate, a second purge interval during which the clean dry compressed air is introduced into the balance of the pneumatic system, and a purge or reference sample interval during which the clean dry purge air is re-circulated through the gas sensor and enclosed volume by the pump. This cycle then repeats as many times as desired.

The apparatus will comprise at least two sub-systems of the type shown in FIG. 11, that are all connected in parallel into one system on a production line. It may further comprise a source of clean dry compressed air for a purge, or reference, a contamination detection apparatus, as shown in FIG. 6 but with 10 sets of sensors (for a total of 20 sensors) and associated components rather than the 3 shown. It is constructed so that the system can sample each bottle within one second, allowing the bottle to proceed down the production line, and produce an output classifying the bottle as clean or contaminated within 4 seconds of the bottle being sampled. It also allows the bottle to be rejected at a point further down the production line by using sensors (not shown) to track the progress of the sampled bottles and an ejector mechanism as is well known to those skilled in the art. Each phase of the sequential operations shown in FIG. 16 will now be discussed in detail with reference to FIG. 11 through FIG. 15. Keeping in mind that the operation is a continuously repeating cycle and the starting point chosen for the description is arbitrary.

Fast Sample Interval

Figure 12:
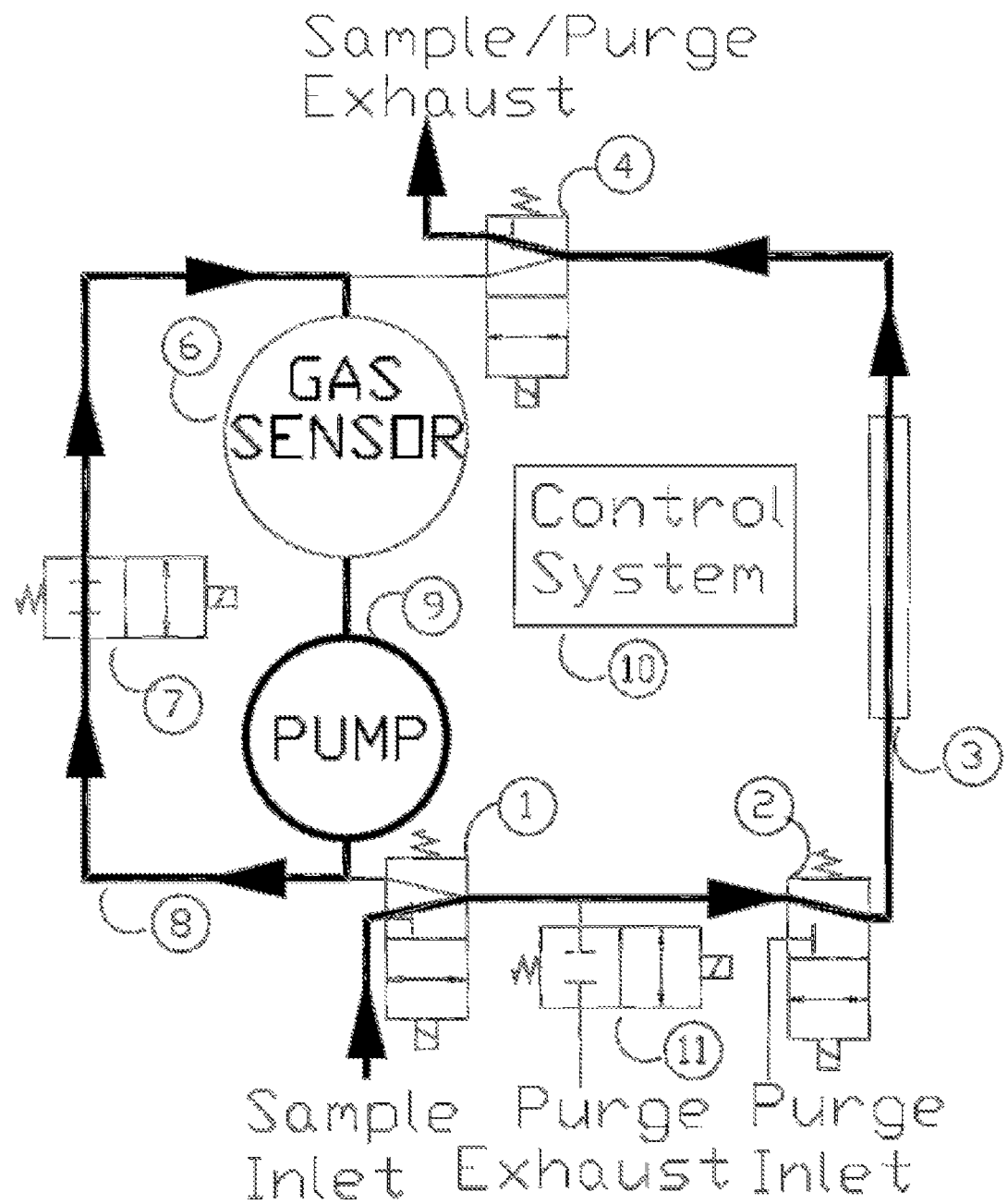
FIG. 12 is a block diagram of the subsystem of FIG. 11 with the gas sample flow illustrated during the fast sampling interval for the illustrated part of the apparatus during which the sample is being transferred to the selected enclosed volume and simultaneously the purge reference air is being re-circulated to complete the recovery or reference interval

FIG. 12 is an example of the flow paths that are enabled when the embodiment is gathering a new sample and re-circulating the purge reference air. During this interval and all intervals the control system 10 controls the valve's positions. Valve 1 is in the position that opens the sample inlet 1 and connects it to the flow path 8. Valve 11 is closed to prevent the loss of the sample being introduced. Valve 2 is in the position that closes the purge inlet and directs the flow through the valve to the enclosed volume 3. Valve 4 is in the position that opens the exhaust outlet and blocks flow to the gas sensor 6. Valve 7 is in the position that opens the valve allowing the purge reference air contained in the gas sensor 6, pump 9 and flow path 8 to continue to re-circulate during the fast sample interval.

Measurement Interval

Figure 13:
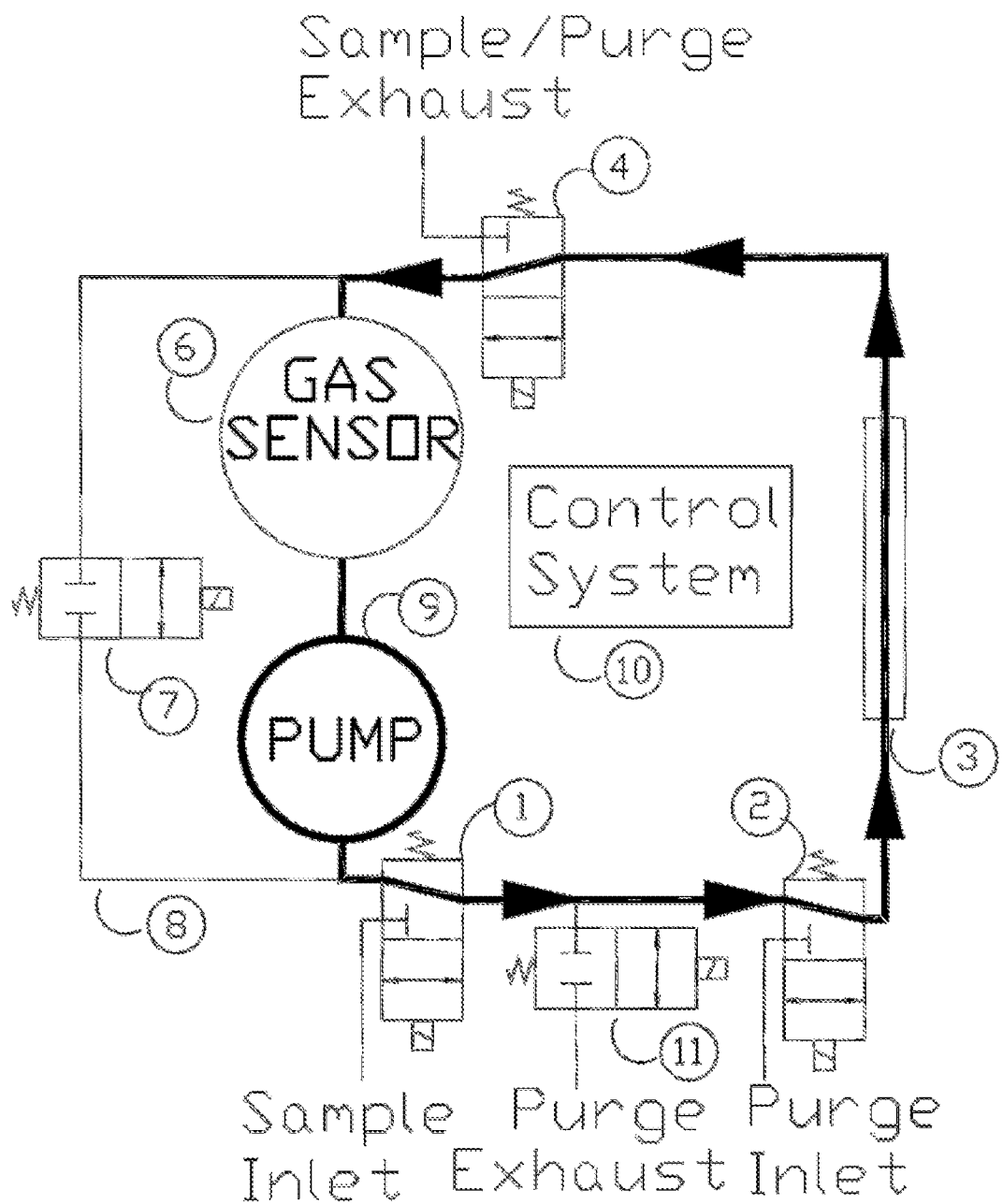
FIG. 13 is a block diagram of the subsystem of FIG. 11 with the gas sample flow illustrated during the measurement time interval for the illustrated part of the apparatus during which the sample is being re-circulated from the enclosed volume to the selected sensor for measurement.

FIG. 13 is an example of the flow paths that are enabled when the embodiment is re-circulating the sample through the gas sensor 6 and enclosed volume 3 using pump 9. During this interval valve 1 is in the position that closes the sample inlet and connects the flow path through valve 1. Valve 11 is closed to prohibit the loss of the sample. Valve 2 is in the position that closes the purge inlet and directs the flow through the valve to the enclosed volume 3. Valve 4 is in the position that closes the exhaust outlet and directs the sample flow to gas sensor 6 and pump 7. Valve 7 could be either closed or open as the small volume in flow path 8 will not significantly affect the sample gas.

Initial or First Purge Interval

Figure 14:
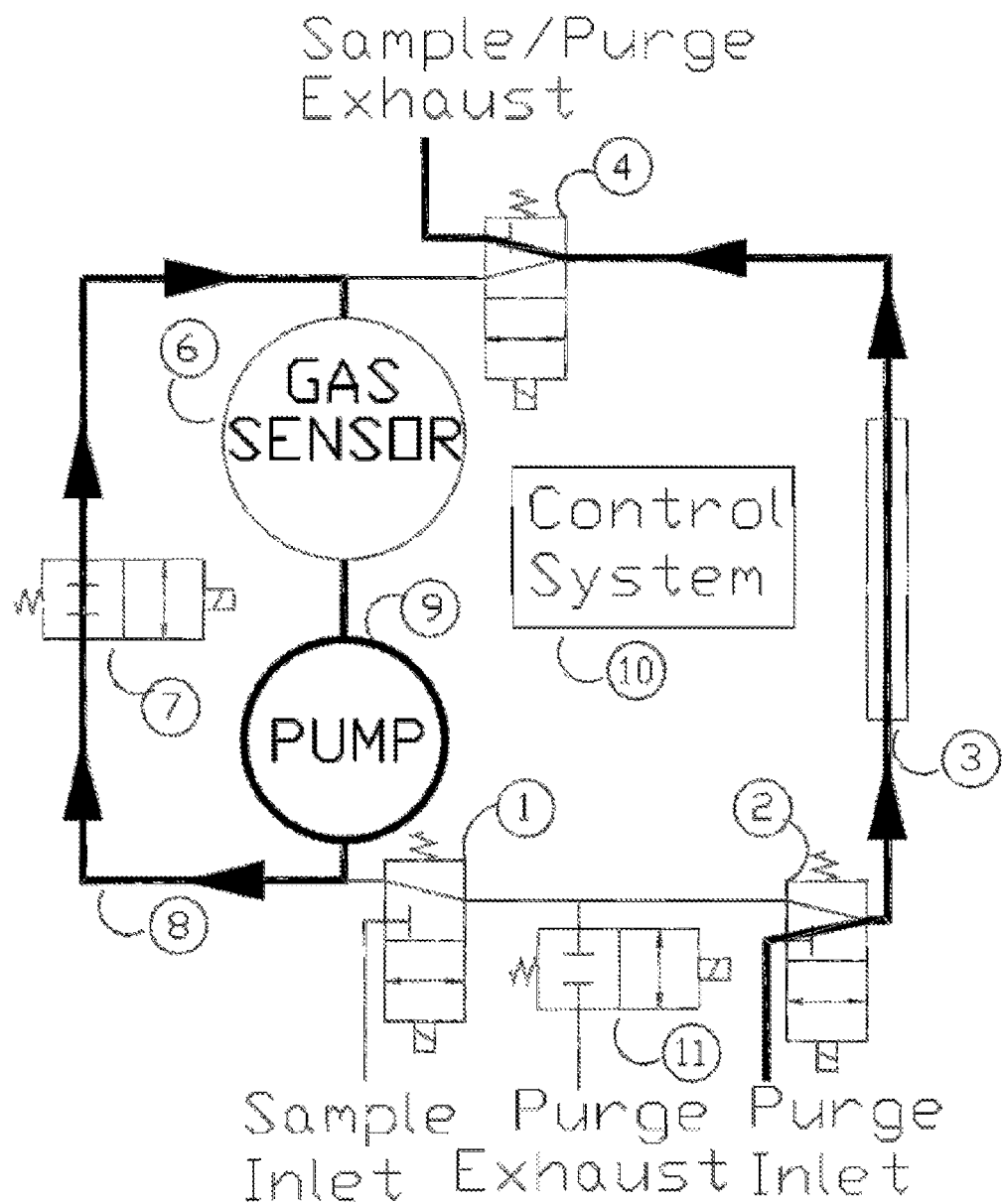
FIG. 14 is a block diagram of the sub-system of FIG. 11 with the gas sample flow illustrated while the sub-system is completing the measurement interval while simultaneously undergoing an initial or first purge reference interval during which the purge or reference gas is introduced to the selected enclosed volume.

FIG. 14 is an example of the flow paths that are enabled when the embodiment is re-circulating the sample gas or vapor through gas sensor 6 using pump 9 to complete the measurement interval while simultaneously allowing clean dry compressed air to flow through valve 2 to enclosed volume 3 in preparation for the purge reference interval. During this interval valve 1 can be in either position since any flow through valve 1 is prohibited by the positions of valve 2 and valve 11. Valve 11 is closed to prevent the loss of the sample. Valve 2 is in the position that opens the purge inlet to the flow path and enclosed volume 3 and closes the flow path from valve 1. Valve 4 is in the position that opens the exhaust outlet and blocks flow of the purge air to the gas sensor 6. Valve 7 is in the position that opens the valve allowing the gas sample contained in the gas sensor 6, pump 9 and flow path 8 to continue to re-circulate and complete the measurement interval during the initial purge interval. At the conclusion of the measurement interval control system 10 receives an analog or digital signal from gas sensor 6 that indicates the status of the sampled bottle, whether clean or contaminated, and either directly or through another supervisory control system causes the ejection of the bottle from the production line if the gas sensor indicates the bottle is contaminated.

Second Purge Interval

Figure 15:
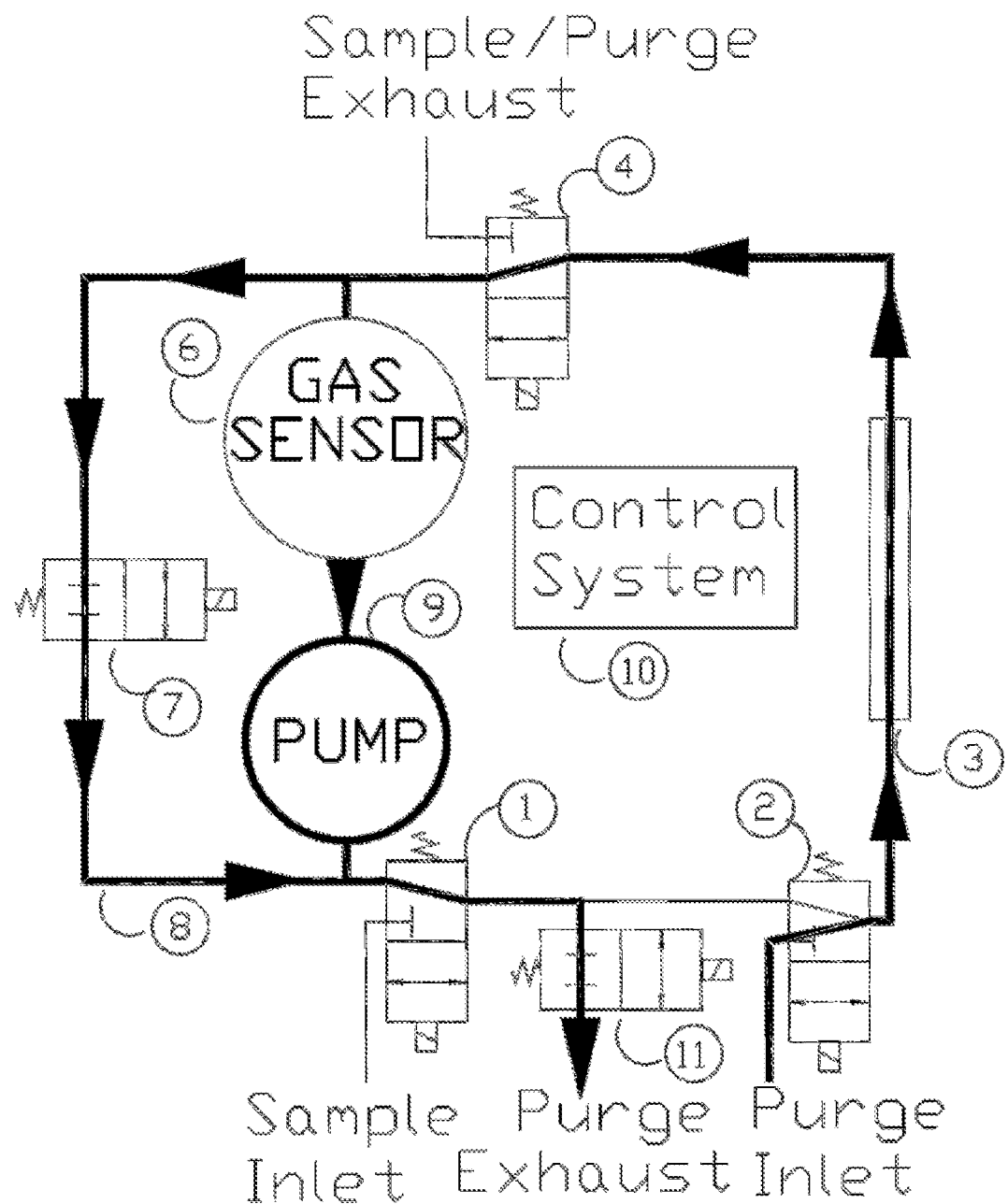
FIG. 15 is a block diagram of the apparatus of FIG. 11 when the system is undergoing a second purge interval during which the purge or reference gas is circulated to the remaining parts of the path to completely remove remnants of the sample.

FIG. 15 is an example of the flow paths that are enable when the embodiment is allowing purge air to flow through the gas sensor 6, pump 9 and the remaining flow path 8 to complete the introduction of purge air during the second purge interval. This is desirable in this embodiment to insure the highest purity of the clean dry compressed air in the apparatus and prevent any contamination from remaining in the gas sensor 6, pump 9 or flow path 8 to disrupt the next sample. During this interval valve 2 is in the position that opens the purge inlet to the flow path and enclosed volume 3 and closes the flow path from valve 1. Valve 4 is in the position that closes the exhaust outlet and directs the purge reference flow to gas sensor 6 and pump 9. Valve 7 is in the position that opens the flow to flow path 8 to purge any remaining sample gas. Valve 1 is in the position that closes the sample inlet and connects the flow path through valve 1. Valve 11 is in the position that opens the purge exhaust allowing clean dry purge air to flow through the entire apparatus.

Figure 17:
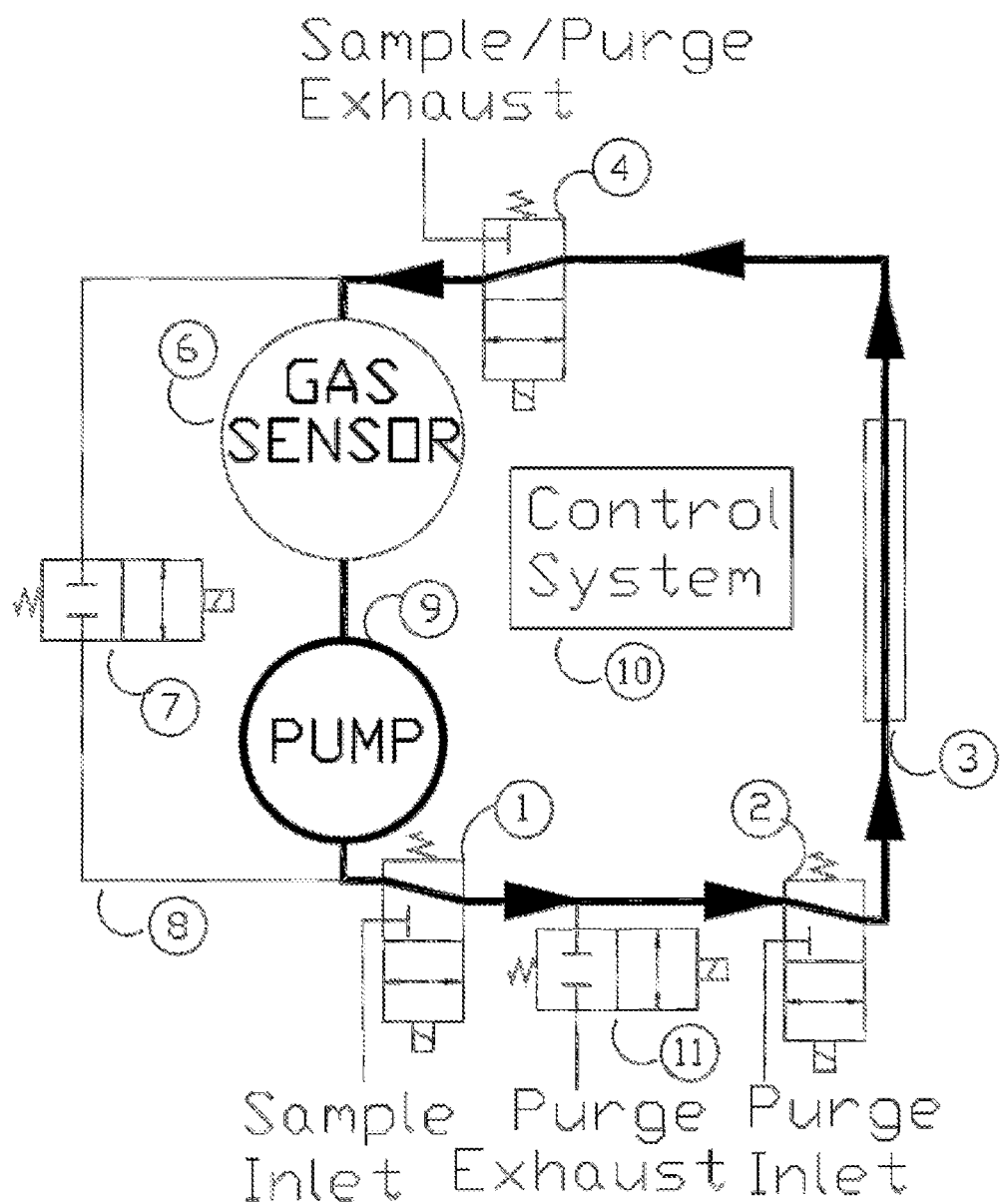
FIG. 17 is a block diagram of the embodiment of FIG. 11 with the gas sample flow illustrated during the recovery or reference time interval for the illustrated part of the apparatus during which the sample is being re-circulated from the enclosed volume to the selected sensor for measurement.

FIG. 17 is an example of the flow paths that are enabled when the embodiment is re-circulating the purge reference air through the gas sensor 6 and enclosed volume 3 using pump 9. During this interval valve 1 is in the position that closes the sample inlet and connects the flow path through valve 1. Valve 11 is closed to prevent the loss of the purge reference air. Valve 2 is in the position that closes the purge inlet and directs the flow through the valve to the enclosed volume 3. Valve 4 is in the position that closes the exhaust outlet and directs the purge reference air flow to gas sensor 6 and pump 9. Valve 7 could be either closed or open as the small volume in flow path 8 will not significantly affect the purge reference gas flow. At the conclusion of the purge reference interval, the control system again returns to the fast sample interval for this one set of measurement apparatus corresponding to the state shown in FIG. 12 and described supra.

It should be understood that minor adjustments can be made to the exact sequence of bringing the various valves to their desired position so as to minimize pressure or flow variations within the apparatus without affecting the essential function of the apparatus or requiring the exercise of the inventive faculty. Also it should be understood that each interval shown could be adjusted to be longer or shorter as required without affecting the essential function of the apparatus or requiring the exercise of the inventive faculty, and that there are other minor adjustments to the operation of the apparatus without affecting the essential function of the apparatus or requiring the exercise of the inventive faculty.

This invention has been described in its presently preferred embodiments and it is clear that it is susceptible to numerous modifications, modes and embodiments within the ability of those skilled in the art and without the exercise of the inventive faculty. Accordingly the scope of the invention is defined by the scope of the following claims. The corresponding structures, materials, acts, and equivalents of all means or step plus function elements in the claims below are intended to include any structure, material, or acts for performing the functions in combination with other claimed elements as specifically claimed.

What is claimed is:

1. A method of detecting one or more chemical components of a gas, vapor, or liquid sample removed from a product on a production line, comprising,
   a. providing an apparatus with at least one subsystem, each subsystem comprising components of:
      i. a sensor operatively configured to detect one or more chemical components of a gas, vapor, or liquid sample removed from a product on a production line;
      ii. a pump operatively configured to circulate the gas, vapor, or liquid sample over the sensor and throughout the subsystem;

iii. an enclosed volume operatively configured as a reservoir for temporarily storing the gas, vapor, or liquid sample;

iv. a plurality of valves under the directional operation of a computerized control system, the valves comprising:

at least one sample inlet valve able to receive the gas, vapor, or liquid sample removed from a product on a production line;

at least one purge inlet valve able to receive a reference sample comprising the one or more chemical components or an agent able to cleanse the subsystem;

at least one exhaust valve configured to release the gas, vapor, or liquid sample or the reference sample, or portions thereof, from the apparatus;

at least one valve configured to direct the flow of the gas, vapor, or liquid sample or the reference sample throughout the apparatus;

v. the computerized control system comprising a computer central processing unit, a program memory, a variable memory and a plurality of input and output circuits for communicating with and controlling the operation of the apparatus components; and, vi. a tubing configured to circulate the sample throughout the apparatus components;

b. conducting a sampling during a sampling interval comprising, the sample inlet valve directing the gas, vapor, or liquid sample via the tubing into the enclosed volume and releasing an excess amount of the sample through one of the exhaust valves;

c. conducting a sample measurement during a measurement interval on the gas, vapor, or liquid sample comprising, pumping the gas, vapor, or liquid sample from the enclosed volume over the sensor, and electrically transmitting data from the sensor to the computerized control system; and, d. analyzing the data by the computerized control system or the sensor to determine if a desired chemical component or contaminant is present in the gas, vapor, or liquid sample.

2. The method of claim 1, further comprising performing a purge or reference sample operation during a purge or reference sample interval if the sensor requires a recovery period or a reference sample between the sample measurements, comprising opening the purge inlet valve and filling the tubing and components to about maximum capacity with a reference sample while blocking access to the sample inlet valve and the exhaust valve connected to the enclosed volume.

3. The method of claim 2, further comprising performing a recovery or reference operation during a recovery or reference interval if the sensor requires a recovery period or a reference sample between the sample measurements, comprising pumping the reference sample over the sensor, electrically transmitting data from the sensor to the computerized control system; and, analyzing the data to determine the chemical components of the reference sample.

4. The method of claim 1, further comprising rejecting from the production line products comprising an undesirable amount of a chemical component as detected by the sensor from the gas, vapor, or liquid sample taken from the product.

5. The method of claim 1, wherein the at least one subsystem comprises a plurality of subsystems which are lying in parallel on the production line and each subsystem is operating under the direction of the respective computerized control system.

6. The method of claim 5, wherein the apparatus comprises three subsystems.

7. The method of claim 5, wherein a number of subsystems required is determined by computing a total time and dividing the total time by a fast sample time, and wherein the total time is computed from adding the fast sample time plus a measurement time plus a recovery or reference sample time.

8. The method of claim 7, wherein the apparatus comprises 10 subsystems, wherein the sensor is a gas sensor, the product is a re-useable drinking bottle, and the sample comprises vapor or gas contained in the bottle prior to the bottle being cleaned for refilling with water, and the apparatus is able to test 1 bottle sample per second and analyze the sensor sample data within about 4 seconds from taking the sample from the bottle.

9. The method of claim 1, wherein the product is a re-useable water bottle, and further comprising injecting compressed air into the re-useable water bottle to force the gas, vapor, or liquid sample into the sample inlet valve.

10. The method of claim 8, further comprising a first purging during a first purge interval occurring concurrently with the measurement interval, and comprising opening the purge inlet valve and filling the tubing and components to about maximum capacity with clean dry compressed air while blocking access to the sample inlet valve and the exhaust valve connected to the enclosed -volume.

11. The method of claim 10, wherein each subsystem further comprises a purge exhaust valve able to release the clean dry air from the subsystem, and the method further comprising a second purging during a second purge interval comprising opening the purge exhaust valve to release the clean dry compressed air after it has purged the sensor of contaminates, and then closing the purge exhaust valve while pumping the dry compressed air throughout the subsystem.

12. The method of claim 11, further comprising performing a recovery or reference operation during a recovery or reference interval comprising pumping the reference sample over the sensor, electrically transmitting data from the sensor to the computerized control system; and, analyzing the data to determine the chemical components of the reference sample, wherein the recovery or reference interval occurs concurrent with the second purge interval.

13. The method of detecting of claim 1, wherein the plurality of valves comprises, one sample inlet valve able to receive the sample removed from a product on a production line;

one purge inlet valve able to receive a sample of a reference of the one or more chemical components, or an agent able to cleanse the subsystem;

two exhaust valves configured to release the product sample or the reference sample, or portions thereof, from the apparatus, comprising one exhaust valve connected to the enclosed volume and one connected to the pump; and three uni-directional valve(s) configured to direct the flow of the sample or reference throughout the apparatus.

14. The method of detecting of claim 13, wherein the two exhaust valves comprise, one exhaust valve connected to the enclosed volume and one exhaust valve connected to the pump.

* * * * *